United States Patent [19]

Chang et al.

[11] Patent Number: 5,457,257
[45] Date of Patent: Oct. 10, 1995

[54] ISOPARAFFIN/OLEFIN ALKYLATION WITH MINIMAL ACID INVENTORY

[75] Inventors: Clarence D. Chang, Princeton; Paul G. Rodewald, Rocky Hill, both of N.J.

[73] Assignee: Mobil Oil Corporation, Fairfax, Va.

[21] Appl. No.: 243,421

[22] Filed: May 13, 1994

Related U.S. Application Data

[63] Continuation of Ser. No. 50,793, Apr. 22, 1993, abandoned.

[51] Int. Cl.$^6$ .................................................. C07C 2/62
[52] U.S. Cl. ........................... 585/724; 585/725; 585/726
[58] Field of Search .................................... 585/724, 725, 585/726

[56] References Cited

U.S. PATENT DOCUMENTS

| | | | |
|---|---|---|---|
| 2,296,370 | 9/1942 | Slotterbeck | 196/10 |
| 2,296,371 | 9/1942 | Slotterbeck et al. | 196/10 |
| 2,345,095 | 3/1944 | Bruner et al. | 260/683.4 |
| 2,452,166 | 10/1948 | Vermillion | 585/725 |
| 2,804,491 | 8/1957 | May et al. | 260/683.4 |
| 2,939,890 | 6/1960 | Hervert et al. | 260/671 |
| 3,131,230 | 4/1964 | Hervert et al. | 260/671 |
| 3,251,902 | 5/1966 | Garwood et al. | 260/683.64 |
| 3,467,728 | 9/1969 | Hervert | 260/683.2 |
| 3,800,003 | 3/1974 | Sobel | 260/683.49 |
| 3,862,258 | 1/1975 | Huang et al. | 260/683.44 |
| 3,873,634 | 3/1975 | Hoffman | 260/683.44 |
| 3,893,942 | 7/1975 | Yang | 252/411 |
| 3,925,500 | 12/1975 | Wentzheimer | 260/683.44 |
| 3,977,621 | 8/1976 | Huffman | 242/75.5 |
| 4,365,105 | 12/1982 | Morganson et al. | 585/525 |
| 4,394,296 | 7/1983 | Madgavkar et al. | 252/433 |
| 4,795,728 | 1/1989 | Kocal | 502/162 |

*Primary Examiner*—Asok Pal
*Attorney, Agent, or Firm*—Alexander J. McKillop; Dennis P. Santini; Robert B. Furr, Jr.

[57] ABSTRACT

A process for alkylating an isoparaffin with an olefin in the presence of a catalyst comprising HF, $BF_3$, and a hydroxylic promoter wherein the total acid dosage as defined herein is less than about 1 weight percent of the total hydrocarbon reactants and the molar ratio of $BF_3$ to the sum of the moles of HF and hydroxylic promoter is greater than zero and less than about 1.

8 Claims, 3 Drawing Sheets

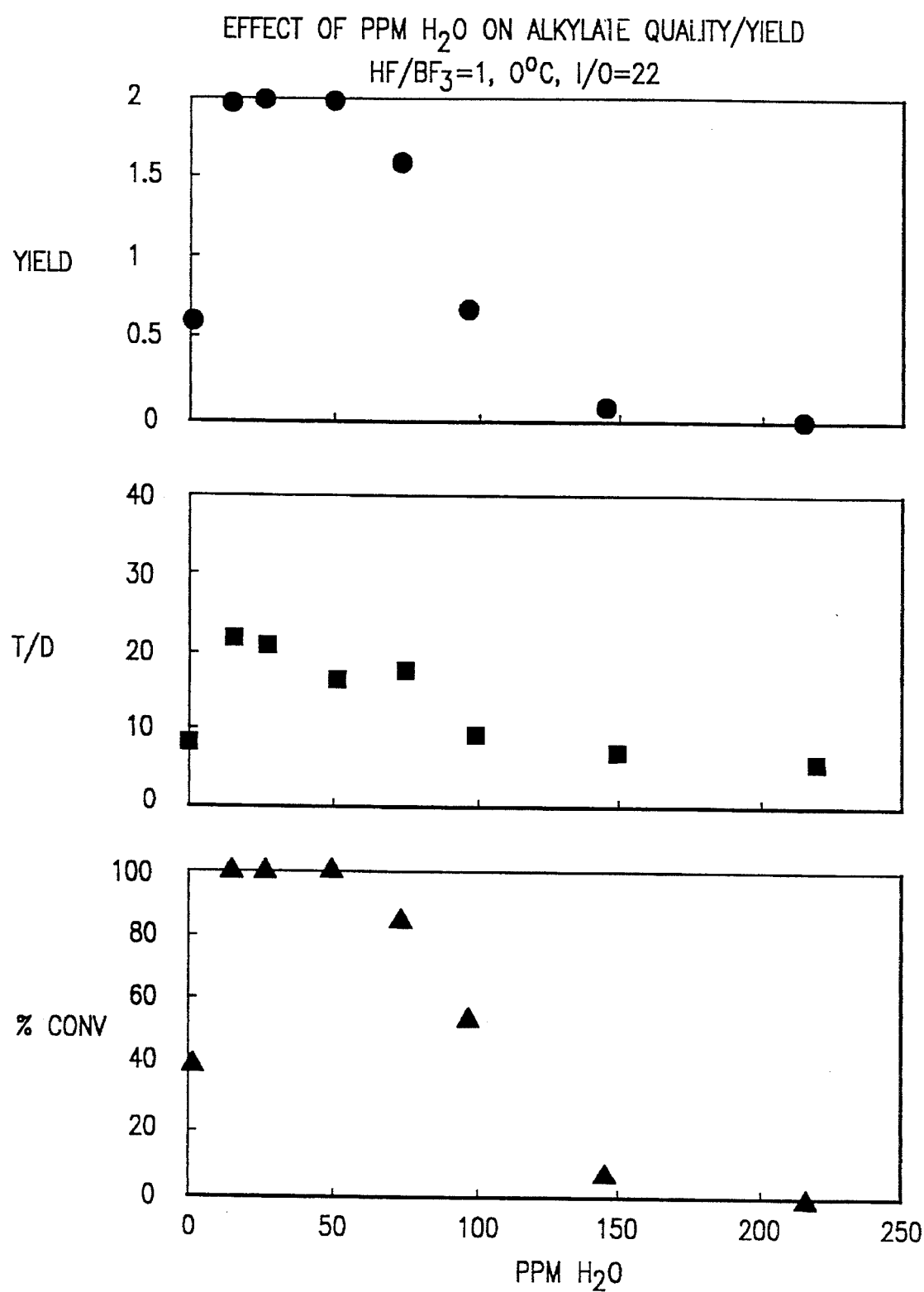

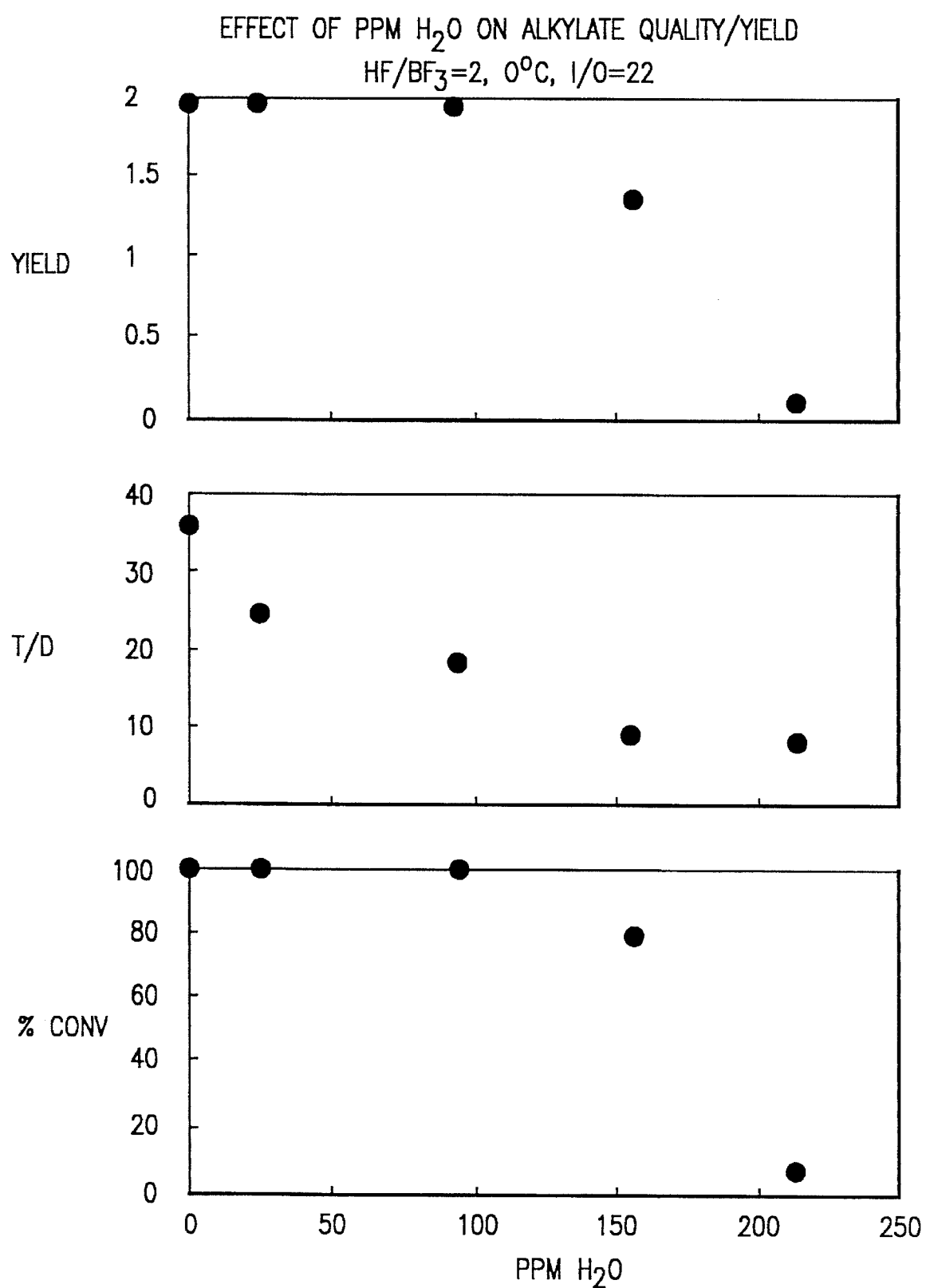

ISOPARAFFIN/OLEFIN ALKYLATION WITH MINIMAL ACID INVENTORY

This is a continuation of application Ser. No. 08/050,793, filed on Apr. 22, 1993, now abandoned.

FIELD OF THE INVENTION

This invention relates to gasoline production. More particularly, the invention relates to a process which produces high octane gasoline by alkylating an isoparaffin with an olefin.

BACKGROUND OF THE INVENTION

Alkylation is a reaction in which an alkyl group is added to an organic molecule. Alkylating an isoparaffin with an olefin yields an isoparaffin of higher molecular weight. The alkylation reaction is of particular interest to the petroleum refining industry because $C_2$ to $C_5$ olefins can react with isobutane in the presence of an acidic catalyst to produce an isoparaffinic product commonly referred to as alkylate. This alkylate is a valuable blending component in the manufacture of gasolines due not only to its high octane rating but also because it is free of aromatics and olefins.

Industrial alkylation processes have historically used hydrofluoric or sulfuric acid catalysts under relatively low temperature conditions. The sulfuric acid alkylation reaction is particularly sensitive to temperature, with low temperatures being favored to minimize the side reaction of olefin polymerization. Acid strength in these liquid acid catalyzed alkylation processes is preferably maintained at 88 to 94 weight percent by the continuous addition of fresh acid and the continuous withdrawal of spent acid. The hydrofluoric acid process is less temperature sensitive and the acid is easily recovered and purified.

Both sulfuric acid and hydrofluoric acid alkylation share inherent drawbacks including environmental and safety concerns, acid consumption, and sludge disposal. Research efforts have been directed to developing alkylation catalysts which are equally as effective as sulfuric or hydrofluoric acids but which avoid many of the problems associated with these two acids. For a general discussion of sulfuric acid alkylation, see the series of three articles by L. F. Albright et al., "Alkylation of Isobutane with $C_4$ Olefins" 27 *Ind Eng. Chem. Res.*, 381–397, (1988). For a survey of hydrofluoric acid catalyzed alkylation, see 1 *Handbook of Petroleum Refining Processes* 23–28 (R. A. Meyers, ed., 1986).

Increasing demands for octane coupled with the increasing environmental concerns have led researchers to seek alkylation processes employing safer, more environmentally acceptable catalyst systems. The goal is to find a commercially viable alternative to the currently used hydrofluoric and sulfuric acid alkylation processes. The following references disclose alkylation catalysts which are alternatives to neat HF.

U.S. Pat. No. 3,862,258 teaches an alkylation process using a catalyst comprising a macroreticular acid cation exchange resin and boron trifluoride. According to the patent, the life of such a catalyst can be extended by the presence in the reaction mixture of closely controlled amounts of water which can be added to the feed as water or as water-forming compound.

U.S. Pat. No. 3,977,621 relates to oligomerization of olefins catalyzed by boron trifluoride which is controlled to yield desired trimer as a dominant lubricant product by adding small amounts of ester together with water or alcohol promoter.

U.S. Pat. No. 4,365,105 also relates to oligomerizing an olefin in the presence of three-component catalyst used in making lubricating oils which comprises a particular silica absorbent with boron trifluoride and water absorbed on the silica.

U.S. Pat. No. 4,394,296 relates to a three-component catalyst used in making lubricating oils which comprises a particular silica absorbent with boron trifluoride and water absorbed on the silica.

U.S. Pat. No. 2,939,890 discloses a process for alkylating an aromatic hydrocarbon with an olefin-acting compound at alkylation conditions in the presence of an alkylation catalyst comprising boron trifluoride-modified alumina. Subsequently, U.S. Pat. No. 3,131,230 discloses the importance of the presence of small amounts of water for maintaining catalyst activity. Both of these patents are limited to aromatic alkylation processes.

U.S. Pat. No. 2,804,491 relates to an isoparaffin-olefin alkylation to make gasoline at temperatures between −20° and 150° F. utilizing a two-component catalyst comprising essentially excess $BF_3$ with a "silica stabilized gel alumina." No activators are taught.

U.S. Pat. Nos. 3,251,902 and 3,893,942, as well as French Patent 1,593,716 and the article by Kirsh and Potts, DIV. OF PET. CHEM. A.C.S. 15, A109 (1970) address alkylation in the presence of zeolite-based catalyst systems.

U.S. Pat. No. 3,467,728 relates to a process for isomerizing olefinic hydrocarbon, such as 1-butene or 1-pentene by contacting the hydrocarbon with a catalyst comprising a crystalline alumina silicate combined with a substantially anhydrous boron halide.

U.S. Pat. No. 3,800,003 relates to a process for producing an alkylation reaction product from an isoparaffinic reactant and an olefinic reactant containing 1-butene, 2-butene and isobutene which includes passing the olefinic reactant through an isomerization zone. The isomerization catalyst comprises a crystalline aluminosilicate combined with a substantially anhydrous boron halide which can be boron trifluoride. Conventional catalysts are utilized for the alkylation reaction and include sulfuric acid and hydrogen fluoride catalyst which have the disadvantages set forth above.

Catalyst complexes comprising $BF_3$ as well as $BF_3:H_3PO_4$ adducts have been proposed, and are discussed in greater detail below. While these catalysts effectively overcome many of the safety and environmental drawbacks of sulfuric and hydrofluoric acid alkylation systems, the volume and quality of $BF_3$ alkylates have not, in the past, proven comparable to that of sulfuric or hydrofluoric acid alkylates. Further, the $BF_3$-catalyzed isobutane/butene alkylation processes typically require high isoparaffin/olefin feed ratios of at least about 5:1 to produce an alkylate gasoline product of acceptable quality.

U.K. Patent 545,441, assigned to Standard Oil Development Company, teaches a $BF_3:H_3PO_4$ catalyzed isoparaffin-olefin alkylation process.

U.S. Pat. No. 2,345,095 to Bruner teaches a paraffin-olefin alkylation process catalyzed by a boron trifluoride-water complex, represented by the formula $BF_3:nH_2O$, where n is preferably from 1 to 1.5.

U.S. Pat. Nos. 2,296,370 and 2,296,371 to Slotterbeck disclose a $BF_3:H_2O:HF$ catalyst system and an isoparaffin-olefin alkylation process employing the same. The catalyst system is said to avoid yield loss due to oxidation of the resulting alkylate product.

U.K. Patent 550,711 teaches a process for increasing the activity of at least partially spent $BF_3:H_2O$ catalyst systems for reuse in an organic condensation reaction. Briefly, the process volatilizes $BF_3$ from the liquid catalyst mass to the extent required to promote separation of a distinct hydrocarbon phase from the catalyst mass. This hydrocarbon phase is then decanted off and fresh $BF_3$ is added to restore catalytic activity.

Canadian Patent 424,000 teaches a process for producing gasoline boiling range hydrocarbons from isobutane and a normally gaseous olefin by absorbing the olefin in phosphoric acid of at least 75 weight percent concentration with an amount of isobutane equal to at least three moles of isobutane per mole of alkyl phosphate in the presence of a catalytic mixture of phosphoric acid and boron halide at temperature between 20° C. and 60° C.

U.S. Pat. No. 3,873,634 to Hoffman teaches a method of increasing the rate of ethylene alkylation by isobutane by carrying out the reaction simultaneously with the alkylation of a small amount of a higher weight olefin with isobutane in the presence of a $BF_3:H_3PO_4$ catalyst complex at low temperature and pressure.

U.S. Pat. No. 3,925,500 to Wentzheimer discloses a combined acid alkylation and thermal cracking process employing a $BF_3:H_3PO_4$ acid catalyst in which unconverted propane and ethane from the alkylation process are converted, for example, to propylene and ethylene which are subsequently alkylated with isobutane to evolve a valuable liquid fuel.

U.S. Pat. No. 4,795,728 to Kocal teaches a hydrofluoric acid catalyzed alkylation process for producing motor fuel. The hydrofluoric acid catalyst complex includes from 0.5 to 5 weight percent of a cationic or anionic surfactant component enabling the process to be operated at an olefin:acid volumetric feed ratio of greater than 1.0 while maintaining acceptable alkylate quality.

SUMMARY OF THE INVENTION

This invention comprises a process for alkylating an isoparaffin with an olefin in the presence of a catalyst comprising HF, $BF_3$, and a hydroxylic promoter. The total acid dosage, defined herein as the sum of the concentrations of the HF and the $BF_3$, must be less than about 1 weight percent of the total hydrocarbon reactants. The molar ratio of $BF_3$ to the sum of the moles of HF and hydroxylic promoter must be greater than zero and less than about 1.

Two critical variables define the window of operation in this process. The first is the weight ratio of total acid to hydrocarbon reactants, and the second is the molar ratio of $BF_3$ to the sum of the moles of HF and hydroxylic promoter. The process of this invention requires catalyst dosage levels which fall below the concentrations required for commercially useful alkylation with convention catalyst systems. While increasing acid dosage in convention HF-catalyzed alkylation improves alkylate quality, high acid dosages are surprisingly detrimental to alkylate quality and olefin conversion in the present process.

BRIEF DESCRIPTION OF THE DRAWINGS

FIG. 2 shows the effect of water concentration (ppm, wt.) on alkylate quality and yield for $HF/BF_3$ ratio of 1 at a reaction temperature of 0° C. and an isoparaffin-to-olefin ratio of 22, Yield, trimethylpentane/dimethylhexane ratio (T/D) and weight percent olefin conversion are plotted as functions of ppm $H_2O$.

FIG. 3 illustrates the effect of water concentration (ppm, wt.) on alkylate quality and yield for $HF/BF_3$ ratio of 2 at a reaction temperature of 0° C. and an isoparaffin-to-olefin ratio of 22, Yield, trimethylpentane/dimethylhexane ratio (T/D) and weight percent olefin conversion are plotted as functions of ppm $H_2O$.

DETAILED DESCRIPTION

Figure 1:
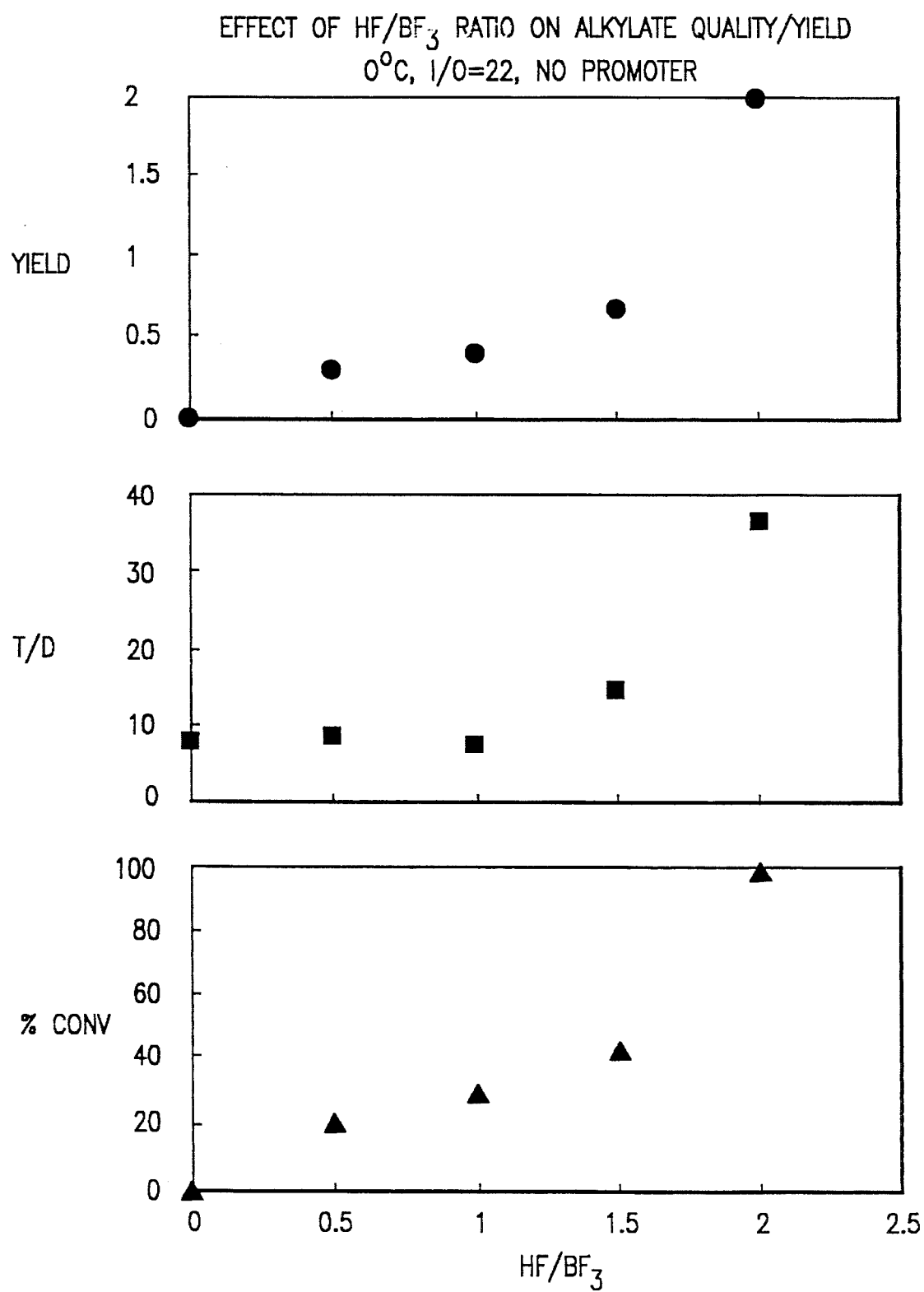
FIG. 1 shows the effect of $HF/BF_3$ ratio on alkylate quality and yield at conversion conditions of 0° C., with an isoparaffin-to-olefin ratio of 22, and no added hydroxylic promoter. Yield, trimethylpentane/dimethylhexane ratio (T/D) and weight percent olefin conversion are plotted as functions of $HF/BF_3$ ratio.

The process of the invention converts a feedstock containing at least one isoparaffin having from 4 to 8 carbon atoms and at least one olefin having from 2 to 12 carbon atoms to a product stream containing a higher molecular weight isoparaffin.

Feedstocks

Feedstocks useful in the present alkylation process include at least one isoparaffin and at least one olefin. The isoparaffin reactant used in the present alkylation process has from about 4 to about 8 carbon atoms. Representative examples of such isoparaffins include isobutane, isopentane, 3-methylhexane, 2-methylhexane, 2,3-dimethylbutane and 2,4-dimethylhexane.

The olefin component of the feedstock includes at least one olefin having from 2 to 12 carbon atoms. Representative examples of such olefins include butene-2, isobutylene, butene-1, propylene, ethylene, hexene, octene, and heptene, merely to name a few. The preferred olefins include the $C_4$ olefins, for example, butene-1, butene-2, isobutylene, or a mixture of one or more of these $C_4$ olefins, with butene-2 being the most preferred. Suitable feedstocks for the process of the present invention are described in U.S. Pat. No. 3,862,258 to Huang et al. at column 3, lines 44–56, the disclosure of which is incorporated by reference as if set forth at length herein.

The weight ratio of isoparaffin to olefin in the total feed to the alkylation reaction zone is generally between 1.5:1 and 100:1, preferably between about 5:1 and about 50:1. Suitable total fresh feedstocks contain isoparaffin and olefin in isoparaffin:olefin weight ratio of from greater than about 1:1 up to about 10:1.

The total feed to the alkylation reaction zone contains both the total fresh isoparaffin/olefin feed and the recycled hydrocarbons from the alkylation reactor including unreacted isoparaffin as well as alkylated product.

The term "recycle ratio" as used herein is defined as follows:

Recycle Ratio=(Weight per unit time Total Hydrocarbon Recycled From the Reactor)/(Weight per unit time of Fresh Feed).

Recycle ratios useful in the present invention typically fall within the range of from about 0.5 to about 100, preferably from about 2 to about 10.

Process Conditions

The present alkylation process is suitably conducted at temperatures of from about –40° to about 500° C., preferably below about 150° C. to avoid undesirable side reactions. Lower reaction temperatures are preferred to maximize alkylate octane. Lower temperatures are generally preferred, for example temperatures as low as −20° C. may be effectively employed. Operating temperature typically falls within the range of about −20° to about 60° C., with the most preferred operating temperatures falling within the range of about −20° to about 30° C.

Operating pressure is controlled to maintain the reactants in the liquid phase, and is suitably from about 50 to about 1500 psig, preferably from about 100 to about 500 psig. The catalyst weight hourly space velocity as well as the total acid dosage may be adjusted within the disclosed ranges by those skilled in the art to optimize alkylate quality and yield for a particular feedstock.

Hydrocarbon and catalyst flow through the alkylation zone is typically controlled to provide weight hourly space velocity (WHSV) sufficient to convert about 99 percent by weight of fresh olefin to alkylate product. Typical WHSV values are detailed below.

The particular operating conditions used in the present process will depend on the specific alkylation reaction being effected. Process conditions such as temperature, pressure, space velocity and molar ratio of the reactants will effect the characteristics of the resulting alkylate, and may similarly be adjusted within the disclosed ranges by those skilled in the art with only minimal trial and error.

Catalyst dosage is critical in this invention. For batch or semi-continuous operation, the amount of catalyst can be expressed as the weight percentage of the total reactants present in the reaction zone. For continuous operation, the fresh catalyst should flow to the reaction zone at a rate approximately equal to the weight percentage of catalyst in the batch operations.

| Catalyst Dosage and Composition Subject to the Constraint, $HF/BF_3 \geq 1$ | | | |
|---|---|---|---|
| Variable | Broad Range | Preferred Range | More Preferred Range |
| R = Ratio of molar concentration of $BF_3$ to the sum of the molar concentrations of HF and the hydroxylic promoter | 0.001 < R < 1 | 0.005 < R < 1 | 0.01 < R < 1 |
| D = Catalyst Dosage as wt. % of total hydrocarbon reactants | 0.01 < D < 1 | 0.03 < D < 1 | 0.05 < D < 1 |

The weight hourly space velocity of the olefin can range from about 0.01 to about 100, preferably from about 0.1 to about 80, and more preferably from about 1 to about 50.

The catalyst can be recovered and/or recycled by any suitable means. Physical recovery methods include distillation as well as separation by differential density including gravitational separation (e.g., decantation) and centrifugal separation (e.g., hydrocyclonic separation). For a survey of design criteria for hydrocyclones, see the four-part series, K. Rietema "Performance and design of hydrocyclones", 15 *Chemical Engineering Science* 298–325, (1961).

The catalyst may also be recovered by sorption with a selective sorbent. The selective sorbents useful in the method of the invention are preferably regenerable, that is, the materials preferably sorb the catalyst under sorption conditions and then release the sorbed catalyst under regeneration conditions so that the sorbent can be reused. From a process standpoint, the sorbent need not be regenerable to be useful, but regenerable sorbents are preferred to minimize waste disposal costs.

The preferred sorbents for the present invention contain no alumina or silica, which may react with HF or $BF_3$ under certain sorption conditions. Similarly, the selective sorbents useful in the method of the invention are preferably essentially free of ions which are exchangeable in the presence of HF or $BF_3$. Sorbents containing exchangeable ions tend to consume the acid components of the catalyst to produce stable salts. Thus activated carbon, poly-vinylpyridine, polysulfone resins, and poly-vinyl alcohols are the more preferred sorbents.

EXAMPLES

The Examples were conducted in semi-batch mode in a stainless steel reactor according to the following general experimental procedure. The reactor was heated to about 150° C. to remove water and then cooled to 0° C. in an ice bath with 4 A sieve dried argon passing through. At this point, a promoter (if used) was injected into the reactor. The HF and $BF_3$ were added to the reactor in one of two different ways, depending upon the total acid concentration used in the experiment. In the experiments using relatively larger amounts of acid, the HF and $BF_3$ were added to the reactor until the desired weight increase was attained. For relatively smaller amounts of acid, the HF and $BF_3$ were added to the reactor using volume calibrated stainless steel vessels using dry $N_2$ pressure.

After the acid was added to the reactor, the reactor was then charged with the desired weight of i-butane, brought to reaction temperature and pressurized to 150 psig. cis- and trans-2-Butene were then charged into the reactor over a typical period of about four hours with stirring at about 1500 rpm. Both the i-butane and the 2-butenes were purified to remove oxygenates by pumping through guard beds containing activated copper chromite, activated alumina, and activated 4 A sieve in sequence.

Upon completion of the 2-butene addition, stirring was continued for 15 minutes. Liquid samples were then taken and analyzed by gas chromatography. These analyses were representative of the total liquid product in the reactor. Light gases were then weathered at 0° C. through a wet test meter to obtain the alkylation product. GC analysis of this product was also conducted.

Examples 1–3

Examples 1–3 demonstrate the criticality of total acid concentration in the process of this invention. Acid composition and promoter dosage were held constant in Examples 1–3. The $HF:BF_3$ mole ratios was held constant at 1:1, and the promoter dosage was held constant at a hydroxide:$BF_3$ mole ratio of 0.06:1. The total acid dosage varied from 670 ppm (Example 1) to 840 ppm (Example 2) to 1000 ppm (Example 3). Butene conversion increased slightly from Example 1 (10 wt. %) to Example 2 (20 wt. %), and then sharply increased to 100 wt. % in Example 3. Alkylate yield behaved similarly, increasing slightly from 0.15 (Example 1) to 0.35 (Example 2), and then sharply to 1.93 (Example 3) based upon a theoretical maximum yield of 2.00. The trimethylpentane/dimethylhexane (T/D) ratio increased more gradually to a high value of 19.2 (Example 3). Results are shown in Table 1.

TABLE 1

Effect of Acid Concentration on i-$C_4$/2-$C_4$ Alkylation
0° C., 150 psig, I/O = 32–35

| Example No. | 1 | 2 | 3 |
|---|---|---|---|
| Total Acid, ppm | 670 | 840 | 1000 |
| Acid composition, molar ratio | | | |
| HF | 1 | 1 | 1 |
| $BF_3$ | 1 | 1 | 1 |
| n-PrOH | 0.06 | 0.06 | 0.06 |
| $C_4^=$ conversion, wt. % | 10 | 20 | 100 |
| Alkylate yield | 0.14 | 0.35 | 1.93 |
| T/D | 3.1 | 8.5 | 19.2 |

Examples 4–10

Examples 4–10 demonstrate the criticality of catalyst composition in the present invention. Table 2 summarizes the results of Examples 4–10. Examples 4 and 5 show that neither HF alone nor water-promoted HF catalyzed the alkylation reaction. Similarly, Examples 6 and 7 show that neither $BF_3$ alone nor water-promoted BF3 catalyzed the alkylation reaction at the total acid dosages of the present invention. Examples 8 and 9 show that a 2/1 molar mixture of HF and BF3 either unpromoted or water-promoted gave 100% butene conversion. The water-promoted catalyst produced a good yield of alkylate (1.88). For the unpromoted catalyst, the alkylate yield was substantially lower at 1.53. While not to limit the scope of the invention by a recitation of theory, this lower yield is believed to be attributable to butene polymerization to $C_9$+ hydrocarbons.

TABLE 2

Effect of Catalyst Composition in i-$C_4$/2-$C_4$ Alkylation
25° C., 150 psig, I/O = 11

| Example | 4 | 5 | 6 | 7 | 8 | 9 | 10 |
|---|---|---|---|---|---|---|---|
| Total acid, ppm | 2300 | 1900 | 3900 | 3900 | 6300 | 5800 | 6200 |
| Acid composition, molar ratio | | | | | | | |
| HF | 1 | 1 | 0 | 0 | 1 | 1 | 1 |
| $BF_3$ | 0 | 0 | 0.5 | 0.5 | 0.5 | 0.5 | 1 |
| $H_2O$ | 0 | 0.06 | 0 | 0.06 | 0 | 0.06 | 1 |
| $C_4^=$ conversion, wt. % | 0 | 0 | 0 | 0 | 100 | 100 | 0 |
| Alkylate yield | 0 | 0 | 0 | 0 | 1.53 | 1.88 | 0 |
| T/D | — | — | — | — | 3.6 | 3.3 | — |

Examples 11–15

Neither HF alone, nor $BF_3$ alone was effective as an isoparaffin-olefin alkylation catalyst under the total acid concentration ranges of the present invention. Examples 4–10 examined the effect of the HF/$BF_3$ ratio on catalyst activity, product quality, and yield. The HF/BF3 ratio was varied from 0 to 2 at 0° C., an isoparaffin/olefin ratio (I/O) of 22, at total acid concentrations of 800–1300 ppm, and with no promoter added. Results are shown in Table 3 and FIG. 1. No butene conversion was observed at HF/$BF_3$=0. As the HF/$BF_3$ ratio increased, butene conversion increased gradually to 100%, and alkylate yield gradually from 0 to 1.97. At HF/$BF_3$=2 and conversion, polymerization is suppressed relative to alkylate by a factor of nearly 40.

Finally, as HF/$BF_3$ ratio increased, the trimethylpentane/dimethylhexane (T/D) ratio increased, reaching a value of 35 at HF/$BF_3$=2.

TABLE 3

Effect of HF/$BF_3$ Ratio on Alkylate Quality/Yield
0° C., I/O = 22, No Promoter
Total Acid 800–1300 ppm

| Example No. | Mole Ratio HF/$BF_3$ | Wt. % Butene Conversion | Yield | T/D | Polymer/Alkylate |
|---|---|---|---|---|---|
| 11 | 0 | 0 | 0 | — | — |
| 12 | 0.5 | 21 | 0.30 | 8.5 | 1.5 |
| 13 | 1.0 | 30 | 0.39 | 7.0 | 2.3 |
| 14 | 1.5 | 43 | 0.66 | 13.8 | 0.84 |
| 15 | 2.0 | 100 | 1.97 | 35.4 | 0.026 |

Examples 16–20

Examples 17–20 examine the effect of four different hydroxylic promoters, while Example 16 (anhydrous acid) is presented as a base case. Results for Examples 16–20 are summarized in Table 4. The four comparison runs were carried out at similar total acid concentration and identical HF/$BF_3$/promoter mole ratios. The addition of water significantly increased the alkylate yield from 1.56 (Example 17) to 1.88 (Example 18). The addition of n-propyl alcohol increased the yield further to 1.94 (Example 18). The additions of methanol (Example 19) and acetic acid (Example 20) had little effect on the alkylate yield and lowered T/D slightly.

TABLE 4

Effect of Promoters on Alkylate Quality/Yield
25° C., I/O = 11

| Example No. | 16 | 17 | 18 | 19 | 20 |
|---|---|---|---|---|---|
| Promoter | None | H2O | n-PrOH | $CH_3OH$ | $CH_3CO_2H$ |
| Total acid, ppm | 6300 | 6400 | 6700 | 6500 | 6600 |
| Acid composition, molar ratios | | | | | |
| HF | 1 | 1 | 1 | 1 | 1 |
| $BF_3$ | 0.5 | 0.5 | 0.5 | 0.5 | 0.5 |
| Promoter | 0.00 | 0.06 | 0.06 | 0.06 | 0.06 |
| $C_4^=$ Conversion, wt. % | 100 | 100 | 100 | 100 | 100 |
| Alkylate yield | 1.56 | 1.88 | 1.94 | 1.49 | 1.58 |
| T/D | 4.9 | 3.3 | 4.8 | 3.8 | 2.6 |

Examples 21–23

Examples 21–33 demonstrate the effect of hydroxylic promoter content on alkylate quality and yield. Examples 21–28 promoter (water) content varied from 0 to 207 ppm. Results for Examples 21–28 are shown in Table 5 and FIG. 2. With no added water, the butene conversion water only 40% and yield was a low 0.62. With the addition of only 12 ppm water, conversion increased to 100% and the yield increased substantially to 1.96. The T/D ratio also advanced from 8 to 21 after the 10 ppm water addition. The addition of 23 ppm and 46 ppm water showed little effect on conversion, yield, or T/D ratio. Further additions of water to 207 ppm resulted in losses in butene conversion ultimately to near 0% with corresponding losses in yield. The T/D ratio dropped to 6–7. At 207 ppm water, the HF, $BF_3$, and water were present in equimolar quantities. Examples 21–28 indicate a window of preferred water concentrations (for HF/$BF_3$ molar ratios of about 1) within the range of about 12 ppm to about 46 ppm which provide high conversion, yield, and T/D ratio.

TABLE 5

Effect of ppm H2O on Alkylate Quality and Yield
HF/BF3 = 1, 0° C., I/O = 22

| Example No. | ppm H2O | Wt. % acid | Wt. % Butene Conversion | Yield | T/D |
|---|---|---|---|---|---|
| 21 | 0 | 0.10 | 40 | 0.62 | 8 |
| 22 | 12 | 0.10 | 100 | 1.96 | 21 |
| 23 | 23 | 0.11 | 100 | 1.98 | 20 |
| 24 | 46 | 0.11 | 100 | 1.97 | 16 |
| 25 | 69 | 0.11 | 85 | 1.60 | 17 |
| 26 | 93 | 0.11 | 54 | 0.69 | 9 |
| 27 | 140 | 0.12 | 7 | 0.09 | 7 |
| 28 | 207 | 0.12 | <0.5 | 0.01 | 6 |

Examples 29–33

Examples 29–33 were carried out at a HF/$BF_3$ ratio of 2, while the hydroxylic promoter (water) content varied from 0 to 207 ppm. Results for Examples 29–33 are shown in Table 6 and FIG. 3. In contrast to Example 21 (anhydrous acid at a HF/$BF_3$ ratio of 1), Example 29 showed 100% olefin conversion with a high yield of 1.97 and a T/D of 35. The addition of 23 ppm water (Example 30) and 92 ppm water (Example 31) showed little effect.

TABLE 6

Effect of ppm H2O on Alkylate Quality and Yield
HF/$BF_3$ = 2, 0° C., 150 psig, I/O = 22

| Example No. | ppm H$_2$O | Wt. % acid | Wt. % Butene Conversion | Yield | T/D |
|---|---|---|---|---|---|
| 29 | 0 | 0.13 | 100 | 1.97 | 35 |
| 30 | 23 | 0.13 | 100 | 1.97 | 24 |
| 31 | 92 | 0.14 | 100 | 1.96 | 18 |
| 32 | 150 | 0.14 | 81 | 1.40 | 9 |
| 33 | 207 | 0.15 | 8 | 0.11 | 8 |

Examples 34–39

Examples 34–39 show the effect of temperature on alkylate quality and yield. Three sets of operating conditions were investigated, each at 0° C. and at 25° C. Results are shown below in Table 7. At 1300 ppm acid, HF/$BF_3$=2, and I/O=20, lowering the temperature from 25° C. to 0° C. significantly increased the alkylate yield from 1.58 to 1.98 and the T/D ratio from 3.6 to 15.5. At a higher 2600 ppm acid, HF/$BF_3$=2, and I/O=10, lowering the temperature from 25° C. to 0° C. again significantly increased the yield from 1.69 to 1.96 and the T/D ratio from 3.6 to 11.1. Finally, at 1000 ppm acid, HF/$BF_3$ ratio lowered to 1, and I/O in the range of from about 34 to about 28, lowering the temperature from 25° C. to 0° C. again significantly increased the yield from 1.51 to 1.93 and the T/D ratio from 10.1 to 19.2.

TABLE 7

Effect of Temperature on Alkylate Quality and Yield

| Example No. | 34 | 35 | 36 | 37 | 38 | 39 |
|---|---|---|---|---|---|---|
| Temperature, °C. | 25 | 0 | 25 | 0 | 25 | 0 |
| I/O | 20 | 20 | 10 | 10 | 34 | 28 |
| Total acid, ppm | 1300 | 1300 | 2600 | 2600 | 1000 | 1000 |
| Acid Composition, molar ratios | | | | | | |
| HF | 1 | 1 | 1 | 1 | 1 | 1 |
| BF$_3$ | 0.5 | 0.5 | 0.5 | 0.5 | 1 | 1 |
| H$_2$O | 0.06 | 0.06 | 0.06 | 0.06 | — | — |
| n-PrOH | — | — | — | — | 0.06 | 0.06 |
| C$_4$= conversion, wt. % | 100 | 100 | 100 | 100 | 100 | 100 |
| Alkylate yield | 1.58 | 1.98 | 1.69 | 1.96 | 1.51 | 1.93 |
| T/D | 3.6 | 15.5 | 3.6 | 11.1 | 10.1 | 19.2 |

Example 40

Example 40 shows the product distribution for i-butane/2-butene alkylation carried out at 0° C., HF/$BF_3$/n-PrOH molar ratio=1/1/0.06, 1030 ppm total acid, and I/O=34. The trimethylpentanes in the product were substantially greater than the dimethylhexanes, leading to a T/D value of 17.2. The low $C_9$+ production led to a yield of 1.93, and the measured research octane number for the $C_5$+ product was 99.8.

TABLE 8 i-Butane/2-Butene Alkylation
0° C., HF/$BF_3$/n-PrOH molar ratio = 1/1/0.06,
1030 ppm Acid, I/O = 34, 100% C$_4$ Conversion

| Product Distribution | Wt. % |
|---|---|
| Isopentane | 0.46 |
| 2,3-Dimethylbutane | 1.10 |
| 2-Methylpentane | 0.11 |
| 2,4-Dimethylpentane | 0.99 |
| 2-Methylhexane | 0.05 |
| 2,3-Dimethylpentane | 0.48 |
| 3-Methylhexane | 0.04 |
| 2,2,4-Trimethylpentane | 51.29 |
| 2,5-Dimethylhexane | 2.01 |
| 2,4-Dimethylhexane | 2.19 |
| 2,2,3-Trimethylpentane | 1.10 |
| 2,3,4-Trimethylpentane | 17.67 |
| 2,3,3-Trimethylpentane | 13.78 |
| 2,3-Dimethylhexane | 0.38 |
| 3,4-Dimethylhexane | 0.35 |
| 2,2,5-Trimethylhexane | 1.19 |
| C$_9$+ | 6.81 |
| Total | 100.00 |

Changes and modifications in the specifically described embodiments can be carried out without departing from the scope of the invention which is intended to be limited only by the scope of the appended claims.

What is claimed is:

1. A process for alkylating an isoparaffin with an olefin in the presence of a catalyst comprising HF, $BF_3$, and a hydroxylic promoter wherein the total acid dosage as defined herein is less than about 1 weight percent of the total hydrocarbon reactants, the molar ratio of $BF_3$ to the sum of the moles of HF and hydroxylic promoter is greater than zero and less than about 1, the molar ratio of HF to $BF_3$ is equal to or greater than about 1, and the weight ratio of isoparaffin to olefin in the feed is from about 5:1 to about 100:1.

2. The process of claim 1 wherein said total acid dosage is from about 0.03 to about 1 weight percent of the total hydrocarbon reactants and said molar ratio of $BF_3$ to the sum of the moles of HF and hydroxylic promoter is from about 0.005 to about 1.

3. The process of claim 2 wherein said total acid dosage is from about 0.05 to about 1 weight percent of the total hydrocarbon reactants and said molar ratio of $BF_3$ to the sum of the moles of HF and hydroxylic promoter is from about 0.05 to about 1.

4. The process of claim 1 wherein said hydroxylic promoter is at least one selected from the group consisting of carboxylic acids, alcohols, and water.

5. The process of claim 1 further comprising at least two hydroxylic promoters selected from the group consisting of carboxylic acids, alcohols, and water.

6. A continuous process for alkylating an isoparaffin with an olefin in the presence of a catalyst comprising HF, $BF_3$, and a hydroxylic promoter wherein the total acid dosage as defined herein is less than about 1 weight percent of the total hydrocarbon reactants, the molar ratio of $BF_3$ to the sum of the moles of HF and hydroxylic promoter is greater than zero and less than about 1, wherein the weight hourly space velocity based upon said olefin is from about 0.01 to about 100, and wherein the weight ratio of isoparaffin to olefin in the feed is from about 5:1 and about 100:1.

7. The process of claim 6 wherein said weight hourly space velocity based upon said olefin is from about 0.1 to about 80.

8. The process of claim 7 wherein said weight hourly space velocity based upon said olefin is from about 1 to about 50.

\* \* \* \* \*